US008615413B2

(12) United States Patent
McKee et al.

(10) Patent No.: US 8,615,413 B2
(45) Date of Patent: Dec. 24, 2013

(54) INTEGRATED ELECTRONIC PATIENT HEALTH CARE AND BILLING COORDINATION SYSTEM

(76) Inventors: John Henry McKee, Dallas, TX (US); Frank Leon Yetter, Plano, TX (US); JoAnne Belcher Klaus, Cocoa, FL (US); Naeem Ahmed Malik, Richardson, TX (US)

( * ) Notice: Subject to any disclaimer, the term of this patent is extended or adjusted under 35 U.S.C. 154(b) by 0 days.

(21) Appl. No.: 13/150,627

(22) Filed: Jun. 1, 2011

(65) Prior Publication Data
US 2012/0041783 A1 Feb. 16, 2012

Related U.S. Application Data

(60) Provisional application No. 61/401,446, filed on Aug. 13, 2010.

(51) Int. Cl.
*A61B 5/00* (2006.01)
(52) U.S. Cl.
USPC .......... 705/3; 705/2; 705/67; 700/2; 700/242; 434/236; 340/572.3
(58) Field of Classification Search
USPC ................. 705/2, 14.67; 707/10; 700/2, 242; 434/236; 340/572.3
See application file for complete search history.

(56) References Cited

U.S. PATENT DOCUMENTS

| 4,860,899 | A | 8/1989 | McKee |
| 5,737,539 | A | 4/1998 | Edelson |
| 5,758,095 | A | 5/1998 | Albaum |
| 5,970,462 | A | 10/1999 | Reichert |
| 5,991,731 | A | 11/1999 | Colon |
| 6,283,761 | B1 * | 9/2001 | Joao .............................. 434/236 |
| 7,107,106 | B2 * | 9/2006 | Engleson et al. ................ 700/2 |
| 7,444,203 | B2 * | 10/2008 | Rosenblum .................. 700/235 |
| 7,698,019 | B2 | 4/2010 | Moncrief et al. |

(Continued)

OTHER PUBLICATIONS

Google patents search result, Sep. 18, 2013.*

(Continued)

*Primary Examiner* — Dilek B Cobanoglu
(74) *Attorney, Agent, or Firm* — Shaukat A. Karjeker; Carstens & Cahoon, LLP

(57) ABSTRACT

A patient care coordination system that includes a plurality of hand-held computers in communication with a cloud computing network or a remote server that has an accessible database of all patients and the health care information of each. The cloud computing network or remote server synchronizes, in real time, patient health care information input in any one of the plurality of hand-held computers with all the others of the plurality of hand-held computers. The hand-held computers are able to download and view the patient health care information in the database in a user friendly graphic user interface equipped with a touch screen for ease of user data navigation. The cloud computing network or remote server also receives, as input, data from patient care devices that are used to monitor patient condition periodically or continuously and store these in the database for the appropriate patient. In addition, the cloud computing network or remote server transmits encrypted electronic digital patient health care information to a third party and receives acknowledgment of third party receipt of the information. The cloud computing network or remote server monitors fee-bearing information exchanged with the third party and automatically assesses a predetermined fee based on fee-bearing information exchanged and stores the billing information to the appropriate patient in the database.

20 Claims, 12 Drawing Sheets

(56) References Cited

U.S. PATENT DOCUMENTS

| | | | |
|---|---|---|---|
| 7,774,097 B2* | 8/2010 | Rosenblum | 700/236 |
| 8,212,677 B2* | 7/2012 | Ferguson | 340/572.3 |
| 2002/0174010 A1* | 11/2002 | Rice, III | 705/14 |
| 2008/0046292 A1* | 2/2008 | Myers et al. | 705/3 |
| 2009/0254572 A1* | 10/2009 | Redlich et al. | 707/10 |
| 2009/0327363 A1* | 12/2009 | Cullen et al. | 707/204 |
| 2010/0305966 A1* | 12/2010 | Coulter et al. | 705/2 |
| 2010/0324728 A1* | 12/2010 | Rosenblum | 700/242 |

OTHER PUBLICATIONS

Google search result, Sep. 18, 2013.*
Brochure, "Envoy Automated Medication System," Jan. 1999, 6 pages, KVM Technologies, Inc., Houston, Texas USA.
Website, Brad Hogenmiller, "RehabCare featured by Apple for iPad/iPhone use in Physical Therapy," SPOT On Chicago, Sep. 13, 2010, 1 page, spotonchicago.com, Chicago, USA.
Website, "Interactive EMR for the iPad," (2011 copyright) 5 pages, ClearPractice, clearpractice.com, USA.
Carol Ukens, "System links nursing home and pharmacy to reduce errors," Drug Topics, Aug. 16, 1999, 1 page, USA.
"New Internet-based System from RNA," ComputerTalk, vol. 19, No. 3, May-Jun. 1999, 1 page, USA.
Gary Schoettmer, "Web Goes Prime Time in Long-Term Care," ComputerTalk, vol. 19, No. 5, Sep.-Oct. 1999, 3 pages, USA.
Advertisement, "RNA Eagle Tap into the Power," p. 55 of ComputerTalk, vol. 20, No. 2, Mar.-Apr. 2000, 2 pages, USA.
Ron Kokot, Presentation to Carrington Health Systems, "Envoy Automated Medication Systems," Dec. 7, 2000, 13 pages, USA.
Advertisement for AMOS, "Its About Time . . . Your Valuable Time," ComputerTalk, vol. 19, No. 5, p. 20, Sep.-Oct. 1999, 1 page, USA.
Minutes, Texas State Board of Pharmacy, Aug. 7-8, 2001, 25 pages, USA.

* cited by examiner

INTEGRATED ELECTRONIC PATIENT HEALTH CARE AND BILLING COORDINATION SYSTEM

RELATED APPLICATIONS

This patent application claims priority from Provisional Patent Application U.S. Ser. No. 61/401,446, filed Aug. 13, 2010.

BACKGROUND

1. Field of the Technology

The technology relates to the creation, management and maintenance of electronic patient health care records, and more particularly to a system including mobile hand-held devices for inputting, coordinating and synchronizing patient health care information, including billing information, in real time, and assessing fees based on services.

2. Description of the Related Art

In recent years there has been an increasing trend in almost all fields of business and in the professions toward maintaining records in electronic form. This form of record retention has several advantages. These advantages include relative ease of updating records, creation of electronic files, and management of large numbers of records, while minimizing manual labor. In addition, in many instances, the frequency of errors and "lost" or misfiled records may be reduced significantly in a well-managed electronic system. Moreover, access to electronic records is facilitated. For example, the person seeking to access records may do so remotely by Internet access to a database that often requires a password authentication protocol that allows appropriate users virtually instant access from any location in the world.

In general, there is a perception that the health care sector has lagged, to some extent, in the adoption and use of electronic records, as compared to the accounting sector, for example. There are many reasons for this lag in the adoption of electronic medical records, including, for example, the upfront costs of conversion to electronic records, the need for care givers (such as doctors and nurses) to be trained and willing to use a system, the cost of conversion for smaller doctors' offices, compatibility between health provider systems and the variety of heath insurance provider systems, and the need to comply with patient confidentiality criteria spelled out in the so-called HIPAA Statute (Health Insurance Portability and Accountability Act of 1996) and Regulations promulgated pursuant to the statute.

SUMMARY

In an exemplary embodiment of the integrated patient health care and billing coordination system the system includes a plurality of hand-held computers in communication with a cloud computing network. The cloud computing network includes a memory with a data base configured to store and update patient health care information. Further, upon receiving data input from any one of the hand-held computers, the cloud computing network synchronizes, in real time, with all others of the plurality of hand-held computers so that users of these may immediately see updated, current data. In addition, the cloud computing network transmits encrypted electronic digital patient health care information to an in-system third party and receives acknowledgment of the in-system third party receipt of the information. The cloud computing network monitors fee-bearing information exchanged with the third party and automatically assesses a predetermined fee based on fee-bearing information exchanged.

In another exemplary embodiment, there is provided a multi-user, automatically synchronized, the integrated patient health care and billing system. The system includes a plurality of wireless hand-held computers and at least one remote server. The remote server, which may be part of a cloud computing system, is in communication with the plurality of hand-held computers in real time. In addition, the remote server has memory including a database configured to store patient health care information. The remote server is also in communication with patient care devices that monitor a patient's condition, such as for example oxygen sensors, blood pressure monitors, cardiac monitors, etc. Upon receiving inputted data, the server synchronizes patient health care information between the pluralities of portable hand-held computers by making newly-input patient health care data received from any one of the plurality of hand-held computers and/or patient care devices substantially immediately available to all others of the plurality of portable hand-held computers. Further, the remote server may be in encrypted electronic digital communication with a third party, transmitting encrypted patient health care information to the third party and receiving acknowledgment of third party receipt of the information. If the third party is an in-system third party, it has capability to access patient health care information from the database on the remote server. The remote server may also automatically assess a fee based on patient health care information communications with the third party.

In a further exemplary embodiment, there is provided a multi-user, automatically synchronized, integrated patient heath care and billing coordination system configured for simultaneous use by a plurality of health care providers. The system includes a plurality of hand-held computers configured with graphic interfaces having graphics displayed thereon. The graphics facilitate health care provider access to patient health care information. In addition, each of the plurality of hand-held computers has wireless communication capability and is in communication with a remote server which may be part of a cloud computing network. The server has memory that includes a database configured to store patient health care information, including billing information. Thus, the server uploads newly-input patient health care information from each of the plurality of hand-held computers to the database in its memory in real time and substantially immediately automatically synchronizes patient health care information between the pluralities of portable hand-held computers. As a result, each of the plurality of hand-held computers accesses the most recent updated patient health care information. Further, the server has encrypted digital communications with a third party to transmit patient health care information and to automatically assess a fee.

BRIEF DESCRIPTION OF THE DRAWINGS

The foregoing aspects and many of the attendant advantages, of the present technology will become more readily appreciated by reference to the following Detailed Description, when taken in conjunction with the accompanying simplified drawings of exemplary embodiments. The drawings, briefly described here below, are not to scale, are presented for ease of explanation and do not limit the scope of the inventions recited in the accompanying patent claims.

DETAILED DESCRIPTION OF EXEMPLARY EMBODIMENTS

Figure 1:
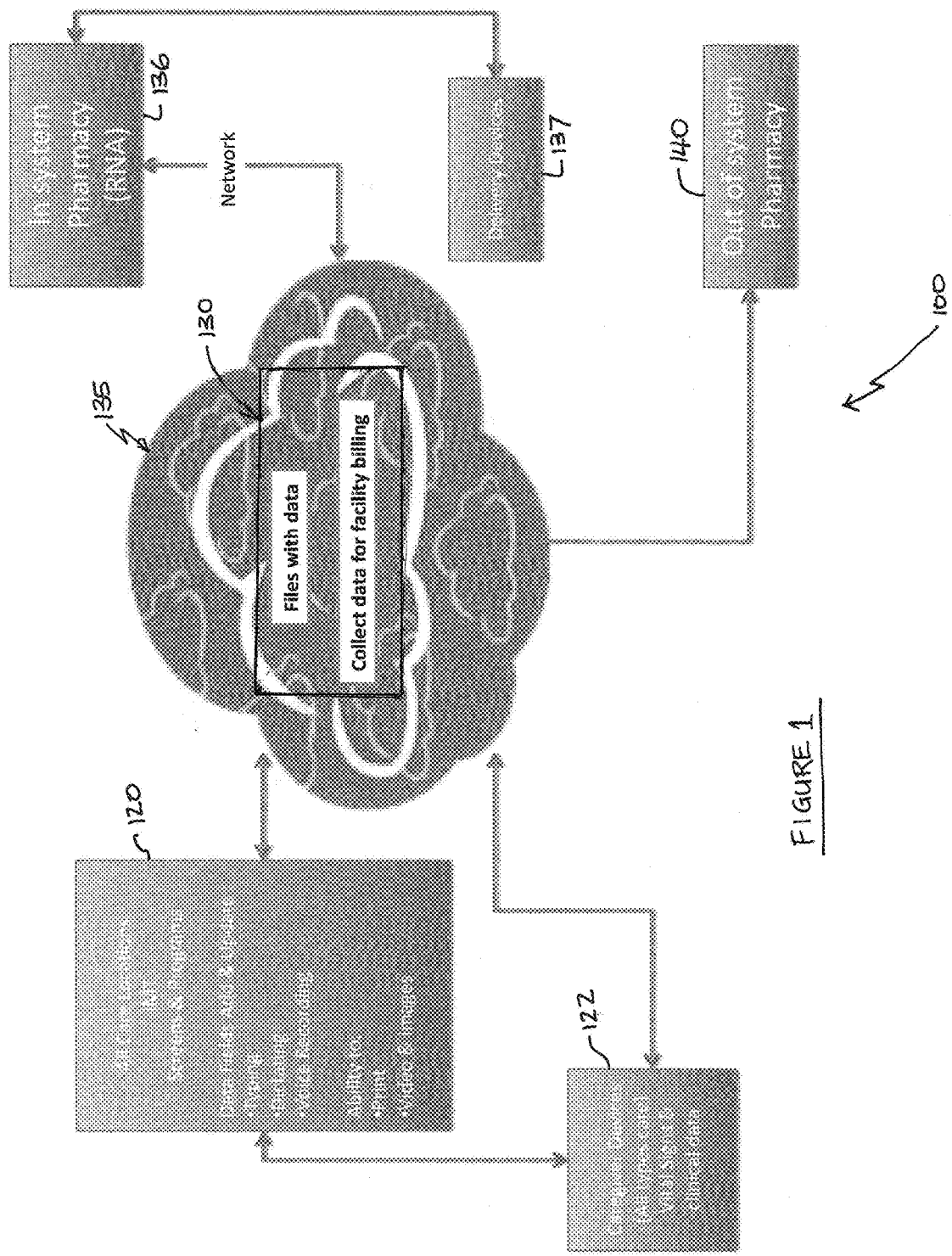
FIG. 1 illustrates a schematic overview of an exemplary integrated, synchronized patient health care and billing coordination system.

The following non-limiting detailed descriptions of examples of embodiments of the invention may refer to appended Figure drawings and are not limited to the drawings, which are merely presented for enhancing explanations of features of the technology. In addition, the detailed descriptions may refer to particular terms of art, some of which are defined herein, as appropriate and necessary for clarity.

The term "patient health care information" as used in the description and the claims of the patent refers to information that may include, but is not limited to, the information about a patient normally kept in the course of his/her treatment by all his/her health care providers, including nurses, physicians, therapist and other care specialists, data received from patient care devices, as well as insurance, billing and accounting information relating to the patient's health care. Such information may include, but is not limited to, prescriptions for pharmaceuticals and other prescribed matter, such as prescribed devices, care giver notes and charts, patient history, laboratory test results, patient care device data (e.g. vital signs including heart rate, EKG, oxygen sensor, and the like, which are monitored in real time) physician orders for medication, and non medication orders to document medications given (e.g. quantity, dose and time given as well as route of administration (oral, inter-muscular)), and other documented results. In short, the term covers everything that involves documenting the care of the patient. In addition, "patient health care information" includes accounting information, such as bills, payments received, amounts outstanding, and insurance information, such as health care insurance carrier, insurance policy coverage details, and the like.

The term "hand-held computer" as used in the description and patent claims refers to a device capable of receiving user input of data, transmitting the data to a synchronizing computer, and receiving data from the synchronizing computer. The device should also be of a size, mass and shape that can be carried with ease by a care giver going about his/her duties, either in the hand of a care giver, or attached to clothing of the care giver, or by some other convenient means that does not significantly impede the care giver in carrying out his/her duties. Accordingly, the term encompasses laptop computers, notebook computers, tablet computers and tablet PCs. In exemplary embodiments, the convenience of a tablet computer, exemplified by the iPad™ (product and trademark of Apple Computer Corp of Cupertino, Calif.), provides some advantages, but other tablet computers may also be useful. But, other hand-held devices may also be included within the term "hand-held computer." These include, but are not limited to, cellular phones, to the extent that these are "smart phones" equipped and configured for data entry, data retrieval, and communication of data to a cloud computing network and/or a remote server either wirelessly via WiFi or through a wireless cellular protocol, such as the 3G and 4G protocols. Smart phones include, for example, the iPhone (product and trademark of Apple Computer Corp. of Cupertino, Calif.), or phones using the Android™ operating system (product and trademark of Google, Mountainview, Calif.), or smart phones offered by other parties with other operating systems. In addition small-format, wireless-enabled devices exemplified by the iTouch (product and trademark of Apple Computer Corp of Cupertino, Calif.) are also included within the term "hand-held computer."

"Cloud computing" refers to Internet-based computing that permits resources to be shared among multiple users and across multiple disciplines. Cloud computing offers an advantage in that an electronic coordinated patient health care system using such computing avoids the upfront costs of buying equipment, and avoids a substantial amount of the ongoing costs of maintaining hardware equipment, while reliability is enhanced due to shared resources that provide backup in the event any one server fails. A description of cloud computing networks may be found at www.Wikipedia.com, for example. Because the technology is known, further description is not deemed necessary here.

Cloud computing is not the only computing means useful in the electronic coordinated patient health care system technology. As an alternative, a remote dedicated server, preferably with backup systems, may also be used, as described here below. The term "remote" in this context may refer to a computer or server located at the same facility where the hand-held computers are in use, or at a different location. Of course, a "remote server" might equally be a server that is part of a cloud computing network.

The term "patient" as used herein is merely for convenience. The systems provided herein are applicable to a variety of facilities such as, for example without limitation, hospitals, assisted living facilities, nursing homes, and home health care organizations. These facilities may apply different terminology to their clients. For example, nursing homes use the term "residents" not "patients." Herein, however, the two terms are used interchangeably. The word "patient" should be read and understood more broadly to include the recipient of health care related services and goods, which includes nursing home "residents."

The term "in-system third party" refers to a third party that has a contractual relationship complying with HIPAA with an owner/operator of the systems according to the inventions, so as to permit access to patient data, with the facility that operates a hospital or nursing home (or assisted living facility, or home health agency, or hospice or other facility providing health care services), but that might not be owned by the hospital or nursing home. An "out-of-system" third party may be a supplier with a contract sufficient to permit receiving information from computer system 400 but that does not have a contractual relationship sufficient to input information to the computer system 400. The out-of-system third party may receive information from computer system 400 via fax or email. Accordingly, an out-of-system third party has no access to patient health care data except as provided by the system for performing a limited task, e.g. to fill, refill or discontinue a prescription, or to provide another service or product for a patient.

FIG. 1 illustrates schematically an overview of an exemplary integrated patient health care and billing data coordination system 100. The particular example relates to a facility, such as a nursing home that is part of a group of nursing homes that may have multiple nursing home locations 120. At the locations 120, care givers have access to hand-held computers and patients may be monitored with patient care devices 122, as explained in more detail here below. Care givers, via the hand-held computers 200 (not shown, but shown in FIG. 2), at locations 120 and patient care devices 122, supply health care information as input data to the patient files in a database 130 that resides either on a dedicated remote server or a cloud computing network 135. As can be seen, the remote server or cloud computing network 135 communicates with an in-system third party 136, in this instance an in-system pharmacy, that receives instructions from the remote server or cloud computing network 135, for example, to fill a prescription for a particular patient, and sends back an acknowledgement as well as other information, such as billing information, which is stored in the database 130, as appropriate for the particular patient. The in-system pharmacy also manages and controls the delivery of the instructed pharmaceutical or other product 137, and notifies the database 130 of the delivery time and expected time of availability of the product at the location 120 for patient use. The illustrated exemplary system 100 may also have the capability to communicate with an "out-of-system" third party 140. In this case, the out-of-system third party 140 is a pharmacy and the information transmitted to it from the remote server or cloud computing network 135 may be a prescription, for example. In the exemplified system 100, the out-of-system pharmacy 140 may not communicate directly back with the database 130 in order to preserve database information integrity and minimize risks of any breach of database security. Instead, the out-of-system party 140 may communicate to a care giver, or designated person, by fax, telephone, text message or email. Thus, the appropriate care giver, at the appropriate location 120, will receive notice of delivery and expected arrival time of any ordered product and can update the database 130 as to these parameters. Appropriate applications software of system 100 can be used to then automatically update the billing information for the ordered product, or the care giver or other designated person may do this manually. In addition, any billing of the third party 140 may also be updated.

As can be seen from FIG. 1, care givers at locations 120 may input data into hand-held computer devices through typing, dictation (speech to text), voice recording (voice files) and video files (photos and video recordings) via hand-held computers 200 (not shown) and upload these to the computer system 135. The care givers may also use the hand-held computers to download data for printing of selected information from the database 130, and to view information for any selected patient. Patient care devices 122 at locations 120 may automatically transmit patient health care data that is uploaded to the computer system 135 for appropriate storing in database 130.

In the example shown, for ease of system use, communications are wireless as far as practicable. Thus, hand-held computers may communicate with the computer system 135 via WiFi or telephony, for example. Patient care devices may have low energy use transmitters such as Bluetooth or RF transmission, for example, and may transmit directly to the computer system 135, or indirectly via transmission to a nearby hand-held computer, which in turn relays the data via WiFi, for example, to the computer system 135 for appropriate updating of the database 130.

Figure 2:
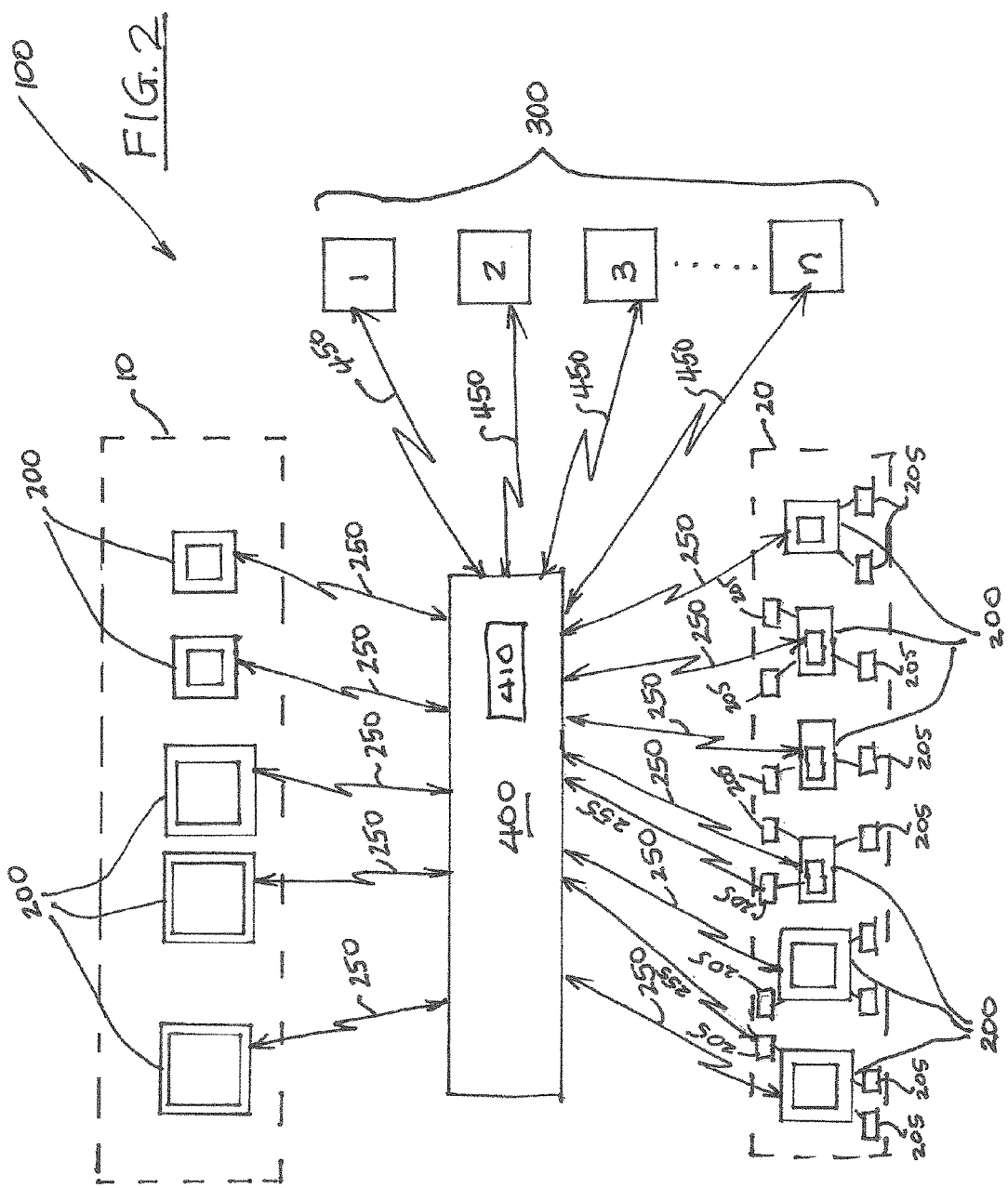
FIG. 2 illustrates in schematic and simplified form an example of the integrated, synchronized patient health care and billing system.

In FIG. 2, an exemplary integrated patient health care and billing data coordination system 100 has a plurality of hand-held computers 200, which are in wireless communication with a synchronizing computer system 400. In the illustrated example, there are two facilities 10, 20 that are each equipped with hand-held computers 200. Clearly, the system 100 is scalable for a plurality of facilities and a plurality of hand-held computers at each facility. The synchronizing computer system 400 may be a cloud computer network, or it may be one or more dedicated remote servers. The synchronizing computer system 400 includes memory 410. Thus, patient health care information input at any of the hand-held computers 200 is uploaded in real time to the memory 410 of the synchronizing computer system 400. The synchronizing computer system 400 then substantially immediately permits the other hand-held computers access to the newly input patient health care information stored in the memory 410. In addition, patient care devices 205 transmit data 255 to the synchronizing computer system 400, or to nearby hand-held computers for transmission to computer system 400. This patient care device data is then immediately synchronized and available to a care giver that might make an inquiry.

Further, the synchronizing computer system 400, when prompted either by a care giver input signal or by pre-scheduled prompt, will communicate through encrypted communications with authenticated (also referred to as "in-system") third parties 300, such as pharmacies, medical doctor offices, insurance companies, and other health care service and product providers to the patients. These authenticated third parties 300 in turn may respond to any communications from the synchronizing computer system 400. Thus, for example, the synchronizing computer system may contact a pharmacy 300 to place a prescription order for a particular patient. The pharmacy 300 may respond with an acknowledgment and a confirmation that it will fill the prescription. Based on this exchange of communications, a fee will be assessed based on the prescription, and charged to the particular pharmacy 300 or medical facility 300 for the service of prescription transmittal. In addition, the system will automatically update both a patient's billing records for all prescriptions, devices, treatments and other billable services provided, as well as his/her insurer's billing records so that a bill may be generated at any time, or at predetermined intervals for payment.

In order to comply with all confidentiality requirements, including the HIPAA Statute (Health Insurance Portability and Accountability Act of 1996), exemplary embodiments provide that communications 250 from the hand-held computers 200 to the synchronizing computer system 400 and communications 450 from this system 400 to the third parties 300 should be encrypted. In exemplary embodiments, the communications 250 are wireless using a Wi-Fi network (i.e.

a class of wireless local area network based on IEEE 802.11 standards). It is expected that Wi-Fi will be updated from time to time, and the present coordinated health care system anticipates adaptation of hand-held computers 200 and synchronizing computer networks 400 to use the best available Wi-Fi platform.

In alternative exemplary embodiments, systems such as mobile 3G or the new 4G (an all IP packet-based system) may be used, instead of Wi-Fi, for communications 250 between 3G or 4G enabled hand-held devices and the synchronizing computer system 400. Such systems are becoming available and may provide the requisite speed of data transfer and data security.

In exemplary embodiments, the encrypted communications 450 between the synchronizing computer system 400 and the in-system third parties 300 may be via the Internet (e.g. as email) to a server at the third party recipient 300, or via facsimile transmission, or by telephony. If the latter, then preferably using an automated telephonic system. Likewise, any return communications 450 from the in-system third party 300 to the computer system 400 (and thence optionally to the hand-held computers 200) may also be via Internet, or by facsimile transmission, or via telephone. In the case of an out-of-system third party, this type of party may respond to a care giver or designated party but may not directly interact with the computer system, other than to receive an instruction from it via the Internet or via telephony.

Technologies for transmission and storage in memory of encrypted data are well known. Accordingly, these encryption technologies will not be discussed in detail. Encryption software may be obtained, for example, from Cisco Systems (San Jose Calif.) and VeriSign (Mountainview, Calif.) as well as other companies.

To maintain system integrity and prevent unauthorized access, the coordinated patient health care system 100 is protected by requiring authentication of all users of hand-held computers 200 and all third parties 300. Authentication of hand-held computer 200 users may be through a password system, or through use of biometrics, such as a finger print reader incorporated into the hand-held device, or in communication with it. Authentication of third parties 300 may be achieved through contractual arrangements with the third parties. Thus, a contract may limit access to transmitted communications 450 to only those authorized to have access, for example, pharmacists. In addition, passwords may be necessary to access email communications 450 that include patient health care information. Responses should likewise be limited to those representatives of the third parties 300 that are authorized to respond.

As is apparent from the foregoing description, one of the features of the coordinated patient health care system 100 is the service of providing needed patient health care information to third parties 300 in a secure manner. The system 100 is monetized by assessing a fee for some services. Thus, for example, when a prescription is transmitted from the synchronizing computer system 400 to a pharmacy 300, and a confirmation response is received, then a fee is assessed for the communication.

In exemplary embodiments, fees may be collected in a variety of ways. For example, a participating third party, such as a pharmacy in the example above, may enter into a contract that obligates it to maintain an account with a balance exceeding a minimum balance. For each fee-bearing transaction, such as a prescription transaction, an automatic deduction is made from the account's balance and transferred to the account of the operator of the coordinated health care system 100. Once the minimum balance is reached, the third party automatically replenishes its account. Other financial arrangements are also possible, of course, such as billing a credit card of the third party pharmacy for each fee-bearing transaction. Services such as PayPal™ (trademark of PayPal Inc. of San Jose, Calif.).

An exemplary embodiment of the system accrues costs and expenses for all billable goods, treatments and services provided for the patient. The system maintains billing entries in a database associated with each patient. Accordingly, bills may be generated at any time, or at predetermined intervals, and provided to the patient and his/her insurer as ebills or in hard copy.

Using the hand-held computers 200 of an exemplary system, a user can make real time updates to a patient's file. Thus, for example, new diagnoses may be recorded on the handheld. These new diagnoses are automatically uploaded to the synchronizing computer system 400 and are available to other users looking at the patient's file. Similarly, hand-held users may input information regarding patient allergies, lab test results, medications, medication administration protocols, treatments, photos of the patient's condition, and any other care orders. The availability in the system of this patient and pharmaceutical drug information enables an automatic cross check of any new prescription against known patient allergies and sensitivities, as well as a cross check for drug interactions, if any with other patient medications. It also permits checking of dosages against pharmaceutical drug information to minimize risks of over/under dosage. Accordingly, the system reduces a number of risks in patient care.

In exemplary embodiments, the hand-held computers may be equipped with any of a variety of useful applications programs. For example, these applications programs may prompt data input by using interrogatories that the user answers to provide the input. In other embodiments, user data input via the hand-held computer may be carried out via handwriting or by scribing with a stylus on a touch screen of a hand-held computer, by voice recording, by typing, by selecting information from a drop down menu, or by dictation. The latter technique may utilize speech recognition products, such as Dragon Naturally Speaking™ (a trademark and product of Nuance of Burlington, Mass.), and the like, to allow verbal input to be converted to text. A medical dictionary applications program may also be provided.

Figure 3:
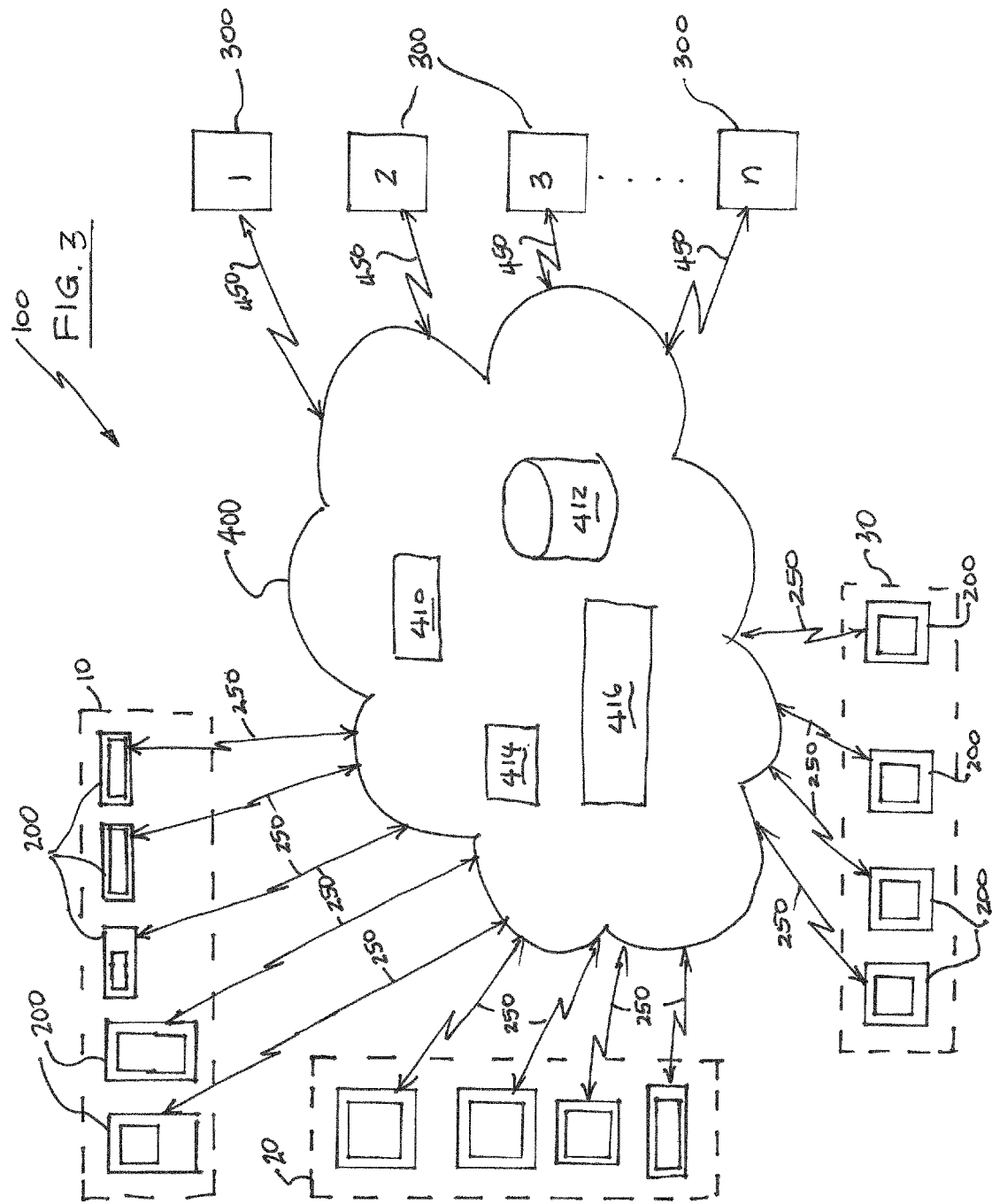
FIG. 3 illustrates in schematic and simplified form an example of an integrated, synchronized patient care coordination system using a cloud computing system.

FIG. 3 illustrates schematically an exemplary embodiment of a coordinated patient health care and billing data coordination system 100 wherein the synchronizing computer system 400 is a cloud computing network 400. In this exemplary embodiment a plurality of hand-held computers 200 are located at each of a first location 10 (for example a first nursing home facility), at a second location 20 (for example a hospital facility) and a third location 30 (another nursing home or hospital, for example). The cloud computing network is dynamically scalable so that a plurality of locations and facilities may be added to the system, as long as the capacity of the coordinated patient health care system 100 is expanded sufficiently to maintain service levels.

In the illustrated coordinated patient health care system 100, the cloud computing network 400 includes several application programming interfaces. Among these is an Internet interface module 410 to enable communications with handheld computers 200 and with third parties 300, a database 412 which constitutes structured cloud "memory" for storage of all patient health care information, and an accounting module 414 that tracks fee-bearing activities, assesses appropriate fees and maintains accounting records of bills and payments. Further applications programs 416 that are not each separately depicted in FIG. 3, may include, but are not limited to, a Speech Recognition applications program, a Calendar applications program, a Clock applications program, a Credit Card applications program, a Wi-Fi applications program, a Communications applications program, a Lexicon applications program, a Camera applications program, a Dialer applications program, a Fax applications program, a Hand Writing Recognition applications program, a Voice Recording Program, a Signature applications program, a Calculator applications program, a Drug Interaction applications program, an EMAR ("Electronic Medical Records") applications program, a Photo applications program, a Printer applications program, a Bar Code Reader applications program, a Bluetooth applications program, a location-based GPS applications program, an MDS program, a RFID applications program, a vascular identification applications program, a retina recognition applications program, a fingerprint recognition applications program, a facial recognition applications program, a CAN applications program, an Inventory applications program, a G/L applications program, a Billing and Payables applications program, an ADT applications program, and any required Interface software that is necessary.

The cloud computing network communicates with a plurality of third parties 300 through encrypted communications 450, as explained above.

Figure 4:
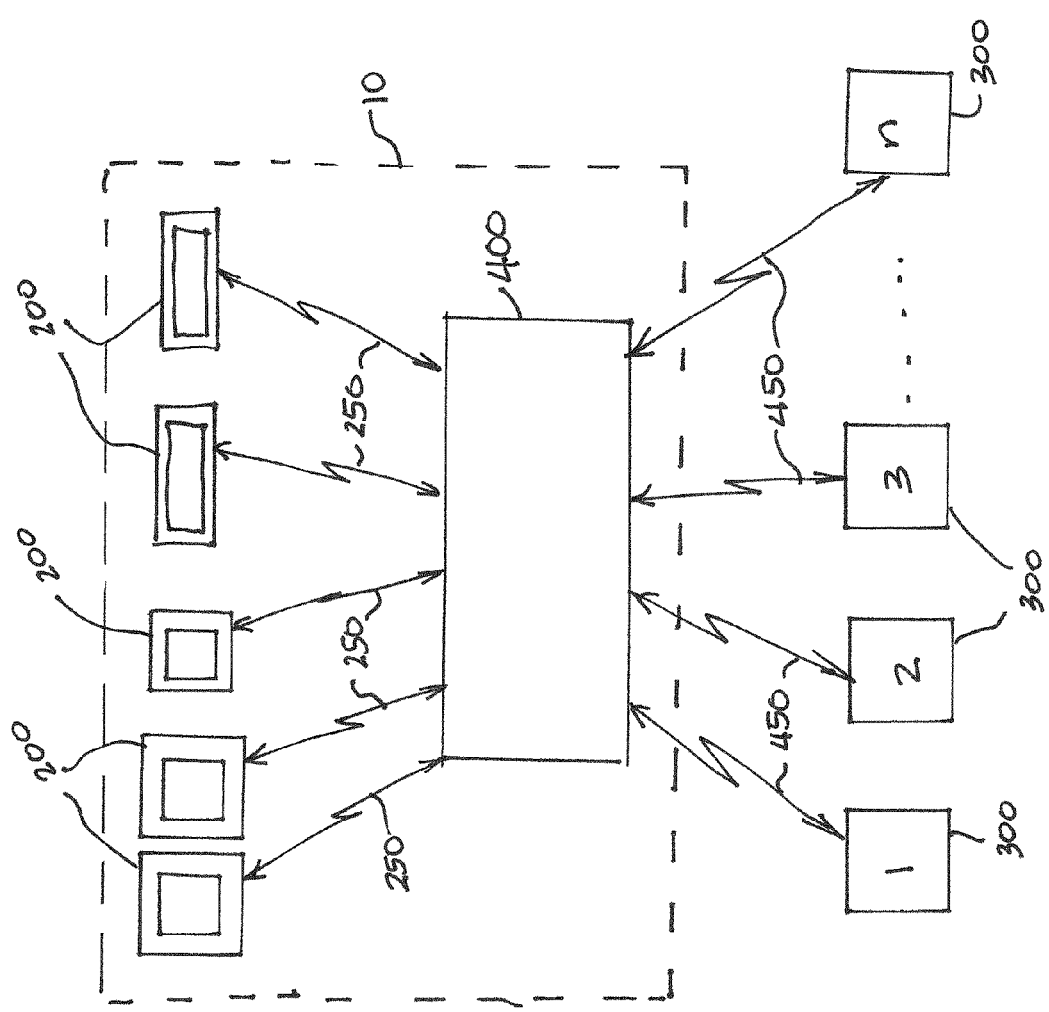
FIG. 4 illustrates an example of a patient care coordination system that has a remote computer system in communication with a plurality of hand-held computers located at a facility, as well as a plurality of third parties.

While cloud computing offers advantages, some facilities may prefer to control the computing hardware in-house and may elect to purchase or lease its own equipment. FIG. 4 illustrates an example of a patient care coordination system 100 that has a remote computer system 400 in communication with a plurality of hand-held computers 200 located at a facility 10, as well as a plurality of third parties 300. In this instance, the computer system 400 may be located on the premises of the facility (e.g., at the nursing home facility 10 that it services) or it may be at a remote location. Further, in an exemplary embodiment, the computer system 400 has appropriate backup of data to prevent data loss, and may also have redundancy in hardware to avoid service interruptions due to potential equipment failures and maintenance downtime.

While not depicted in FIGS. 3 and 4, these exemplary systems 100 may also include patient care devices 205, depicted in the example of FIG. 2, and operating as explained with reference to FIG. 2, above.

Figure 5:
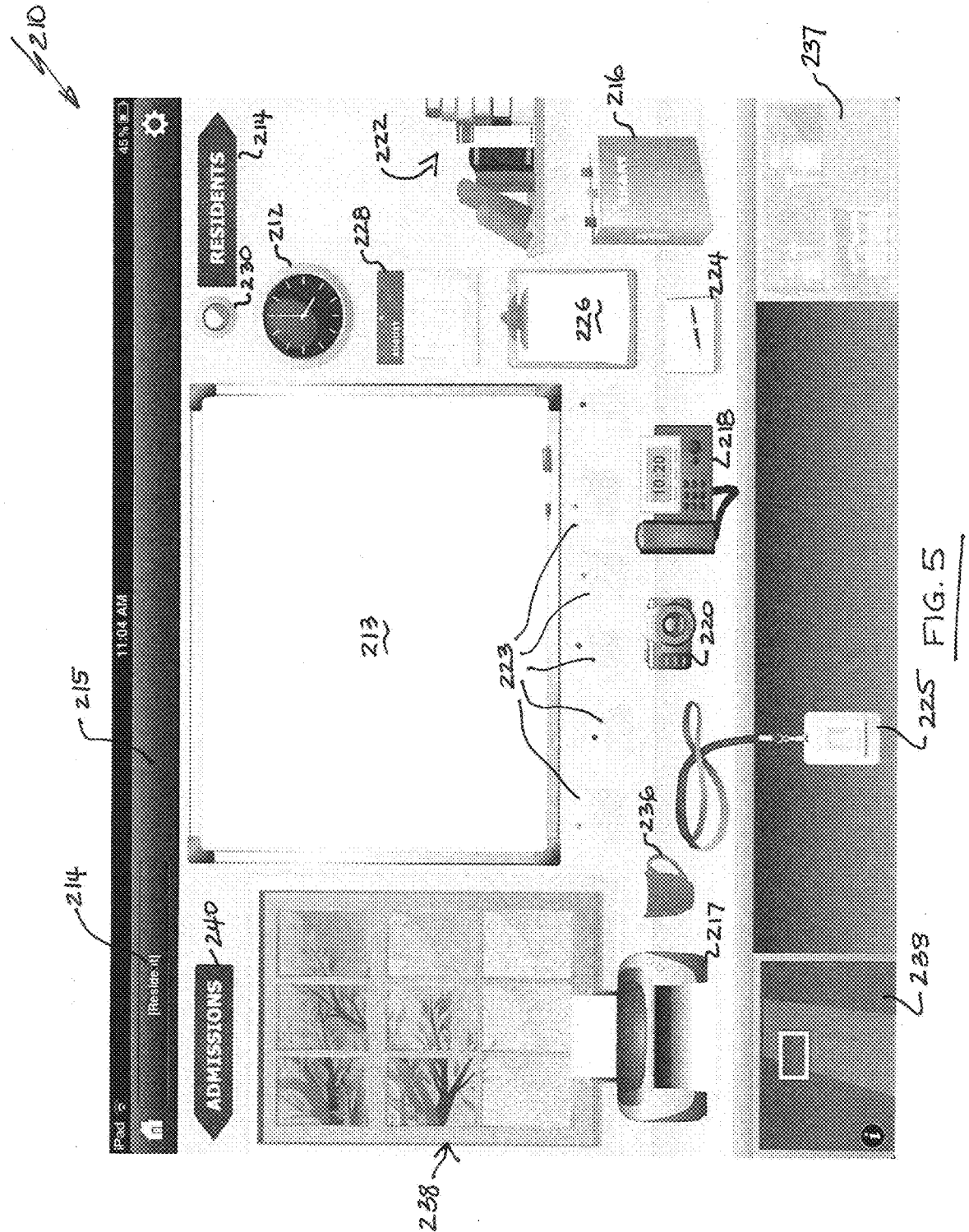
FIG. 5 illustrates an example of an embodiment of a graphic user interface home page on a touch screen of a hand-held computer.

FIG. 5-FIG. 12 each illustrates exemplary graphics that may be included on a touch screen 210 of a hand-held computer 200 of the integrated, synchronized, patient health care and billing data coordination systems 100 for use in a nursing home facility. In the illustrated example, FIG. 5 is a home page with graphics that represent a "nurses' station" and each icon on the screen may be "live." In this exemplary embodiment, the user "drills down" to access information after selecting the appropriate icon initially. The graphic for each icon is selected to readily suggest its function and the data that may be accessed through it. Further, once an icon is selected by "touching" (if a touch screen) or "clicking" (a non-touch screen) on it, it opens a menu or form relating to information suggested by the icon. Additionally, "clicking" or "touching" information on the menu or form, may open yet another screen with additional information based on the selection from the menu.

In the example of FIGS. 5 through 12, a user will log in to the exemplary system 100 using predetermined authentication, such as a user-identification and a password, or biometrics, or some other means of authentication. The hand-held device is then activated and is programmed to provide information to that user, allow that user to input data, and also to access data specific to that user (e.g. health care data regarding a nursing home resident under the care of that particular user). The user may then, for example touch the Clock icon 212, which displays actual time of day. This may also produce a pop-up menu that lists scheduled activities specific to the user. For example, it may list the upcoming "rounds" of the user, listing residents to whom medications and/or treatment must be administered and the time for such administration. The central "white board" icon 213 lists alerts and messages appropriate for the particular care-giver user of the system 100. Thus, once the care giver has logged into the system, and has been authenticated, she can immediately see and review the "white board" icon 213 to see alerts pertinent to her.

Figure 6:
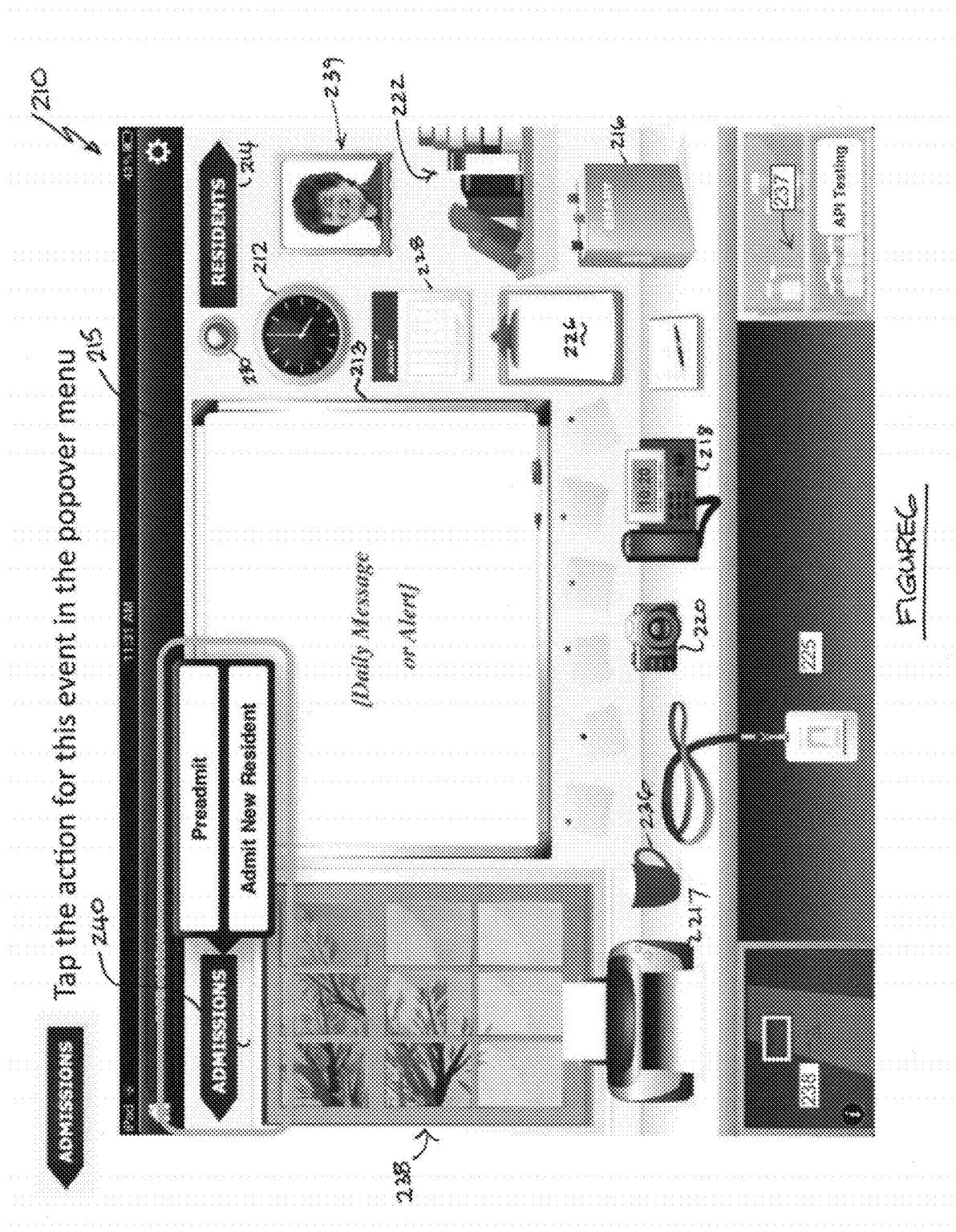
FIG. 6 illustrates an example of an embodiment of a graphic user interface on a touch screen of a hand-held computer graphic user interface.
Figure 7:
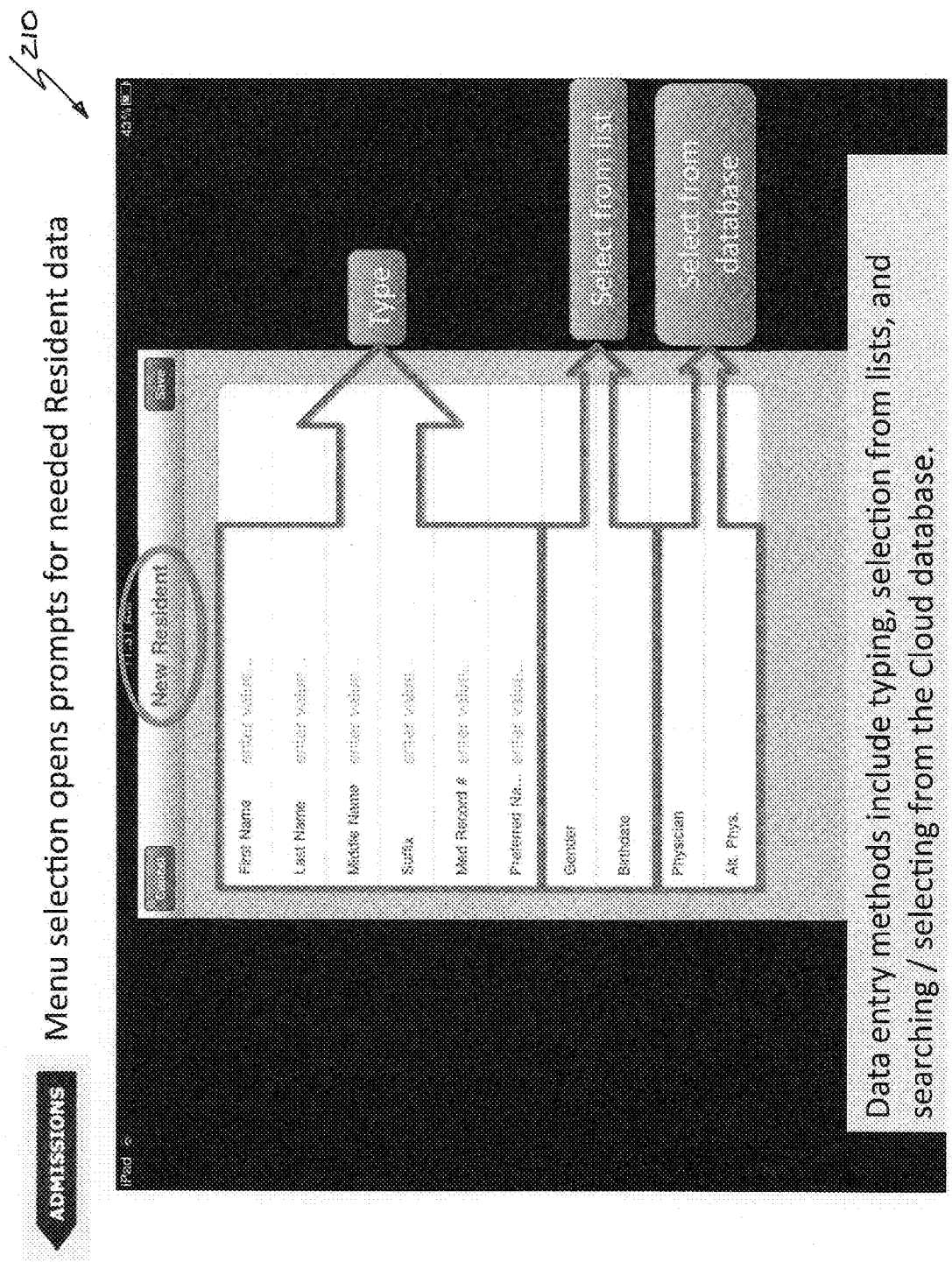
FIG. 7 illustrates an example of an embodiment of a graphic user interface on a touch screen of a hand-held computer.
Figure 8:
FIG. 8 illustrates an example of an embodiment of a graphic user interface on a touch screen of a hand-held computer.

To admit, re-admit or pre-admit a new patient or resident, the care giver touches the admissions icon 240 of FIG. 5 and selects from the drop down menu of choices that appears as shown in FIG. 6. To admit a new resident, she types in required information (name, medical record, etc.) as prompted by a form, as exemplified in FIG. 7. Some data may be selected from menus, like gender, or birth date, for example. The information is readily saved by tapping a "save" button, as shown in FIG. 8.

Figure 9:
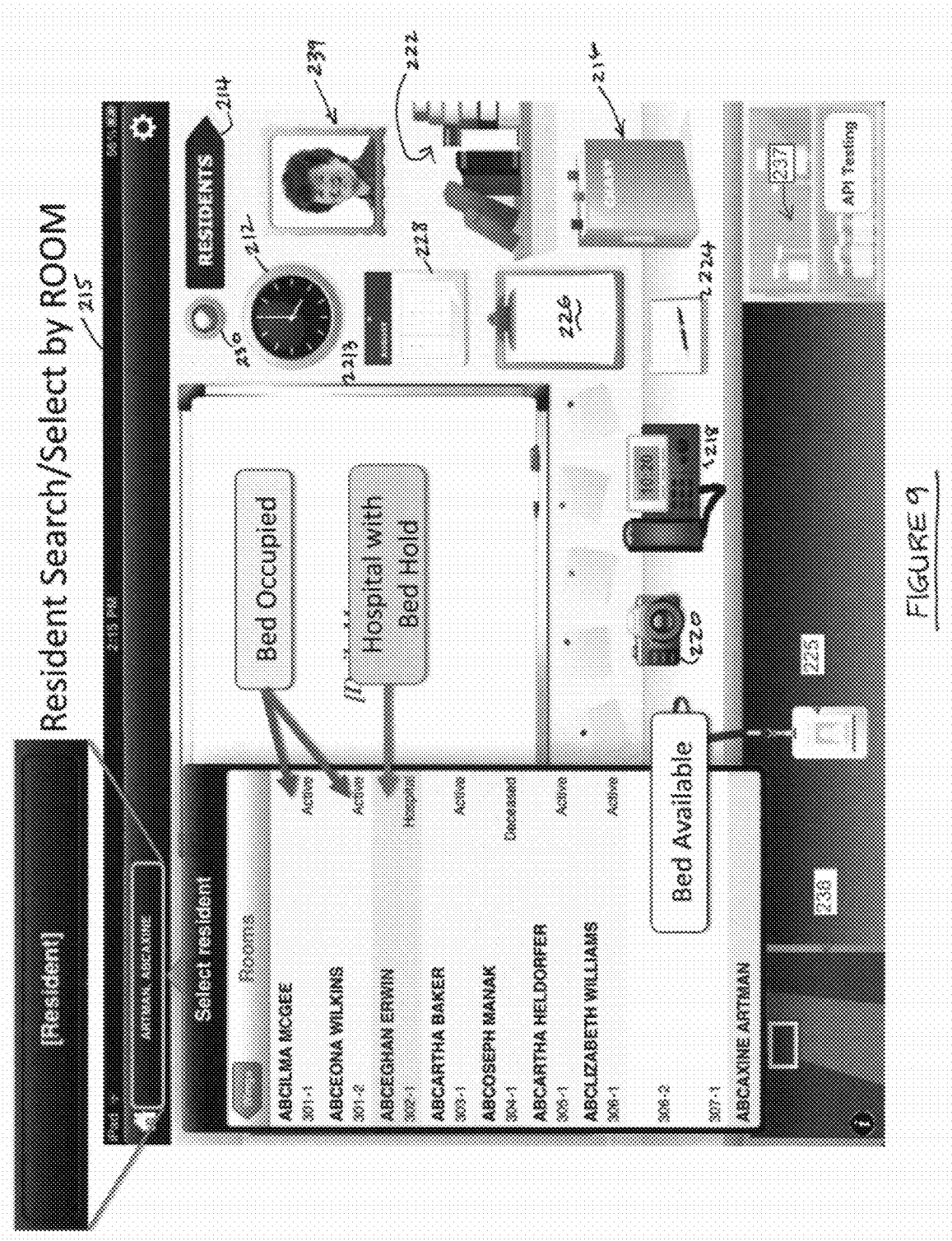
FIG. 9 illustrates an example of an embodiment of a graphic user interface on a touch screen of a hand-held computer.
Figure 10:
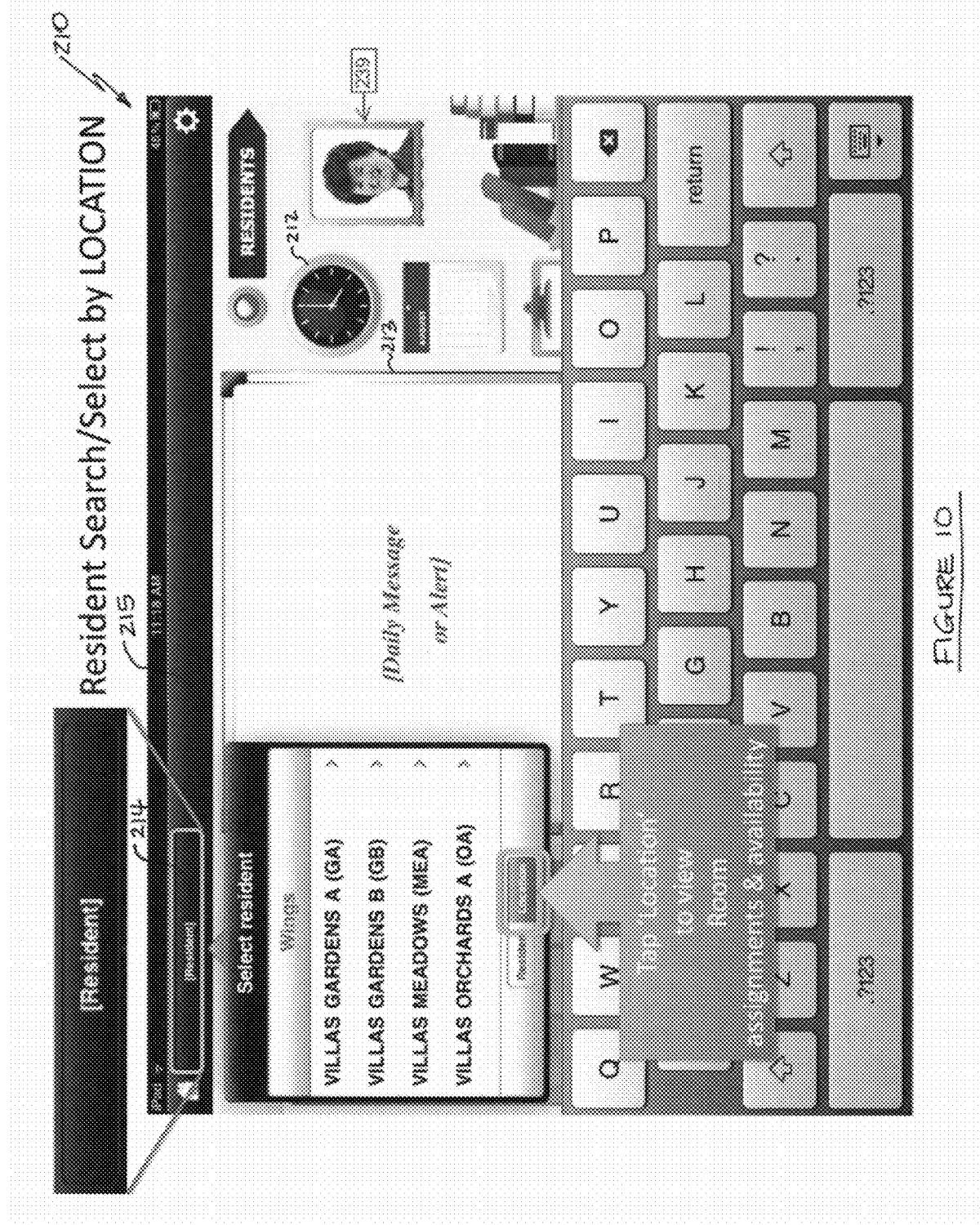
FIG. 10 illustrates an example of an embodiment of a graphic user interface on a touch screen of a hand-held computer.

To find a particular resident, the care giver touches the exemplary "resident" button 214 on the tool bar 215 of FIG. 5 which opens a menu of patient names, as shown in FIG. 9. The care giver may then search for a patient by name (FIG. 9) and/or location and room, as shown in FIG. 10. The listing of residents may be color coded, as shown in FIG. 9, indicating resident status. For example, those that are in urgent need of care may be shown in red and those that are not urgently in need of scheduled medications and treatments may appear in green. Similarly, colors may be used to indicate other status, for example, occupancy status, such as Active, LOA, in Hospital, deceased within a certain time frame, or bed not occupied. Color coding may also indicate those residents that missed getting their treatment or medications.

Figure 11:
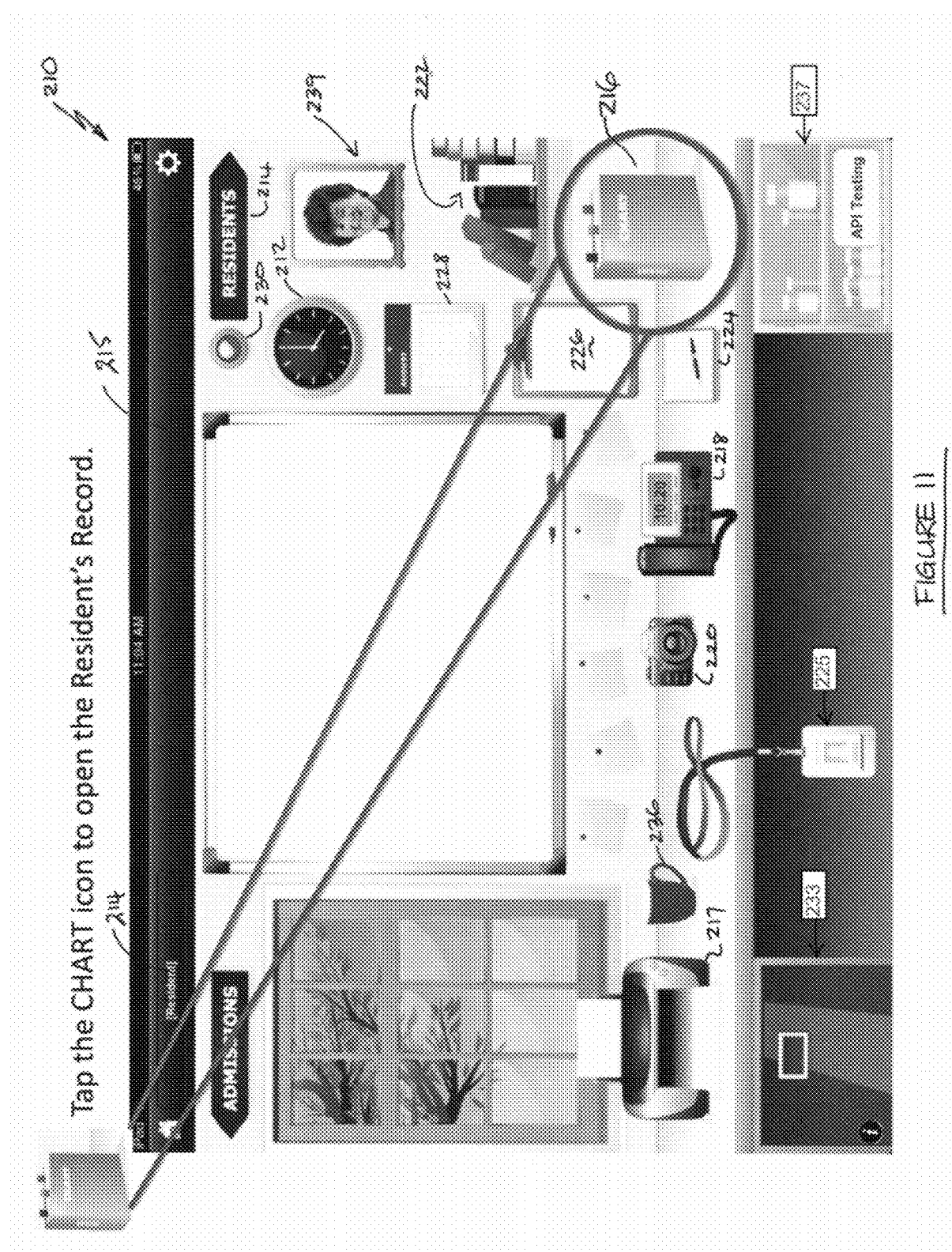
FIG. 11 illustrates an example of an embodiment of a graphic user interface on a touch screen of a hand-held computer.
Figure 12:
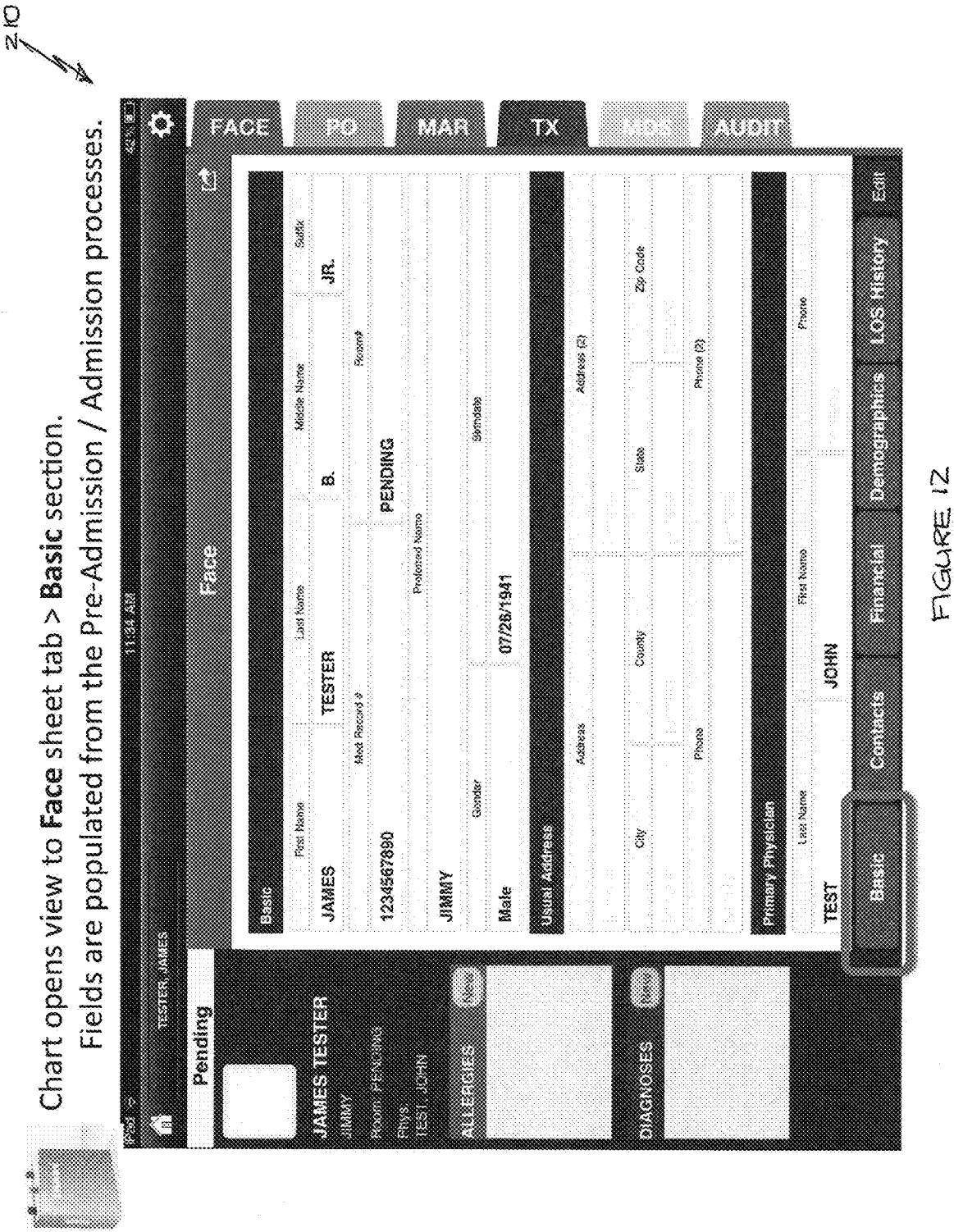
FIG. 12 illustrates an example of an embodiment of a graphic user interface on a touch screen of a hand-held computer.

Upon selecting a particular resident, touching the "chart" icon 216 of FIGS. 5 and 11, the hand-held computer 200 opens a new screen, FIG. 12, that includes pertinent health care information and that may include a photo of the resident to minimize any risk of resident mis-identification. The screen, FIG. 12, lists important resident information, such as pending or overdue treatments, allergies, recent test results, diagnoses, physician data, etc. The screen also has a series of side, color-coded 'touch tabs' as can be readily seen, that permit access to more specific patient information, such as pharmaceutical treatments ("PO"), medical records ("MAR"), therapeutic information ("TX"), Minimum Data Set ("MDS") and any audit data. Along the bottom of the screen, in this example, are arrayed additional touch tabs relating to the resident's contacts, financials, demographics, and LOS history. Importantly, there is also an "edit" touch button 202 that permits the care giver to edit any of the resident's health care information, as allowed by the system.

Referring back to FIG. 5, touching the printer icon 217 permits transmitting information to a printer wirelessly to print out selected information, for example, a prescription for a resident.

Touching the phone icon 218 pulls up a contact list and permits placing a call, text a message or email by touching a desired name or number or email address, as appropriate.

Touching the camera icon 220 activates the camera of the hand-held computer 200 and permits the user to photograph information, for example wounds of a resident.

Touching the "books" icon 222 permits access to reference materials, such as the PDR or other reference selected from the pop-up menu.

Touching the note pad 224 permits the user to input information about a resident.

Touching the clip board 226 allows the user access to notes that a care giver on a prior shift may have left for him/her regarding a resident's condition, requests, or other information.

Touching the calendar 228 pops up the current month or week or day and scheduled activities for that period. Touching the activity provides more information in a new screen or on the same screen.

Touching the "alarm light" 230 when it is flashing provides an urgent alert. That alert may relate to resident condition, fire, or other emergency. It may provide a pop-up menu for the user to select, for example, whether to call code blue, call 911 etc, as necessary.

Touching the coffee cup icon 236 will indicate to all other system users that the user is taking a break.

As personalization, in the exemplary graphic display 210, the user may customize the window scene 238 to any of a number of scenes that he/she finds pleasing.

The filing cabinet icon 233 is intended to be dedicated to management functions.

The ID card icon 225 is intended to be used for user functions.

The "sticky note pads" icons 223 may be used or may be an optional item, for example, and may only appear as necessary or appropriate as alerts to a user.

The "medication containers" icon 237 may be a "live link" that directs to the MAR for the patient to shortcut having to go to that information via the chart icon Optionally, the screen may also include a photo display of the user as icon 239, shown in FIG. 6 (but not FIG. 5), for example.

Exemplary embodiments of the automatically synchronized, patient care coordination system 100 may provide many advantages over the current systems. For example, the coordinated patient health care system substantially replaces paper forms with electronic data that may be accessed in several different ways. This has several resultant benefits including linking medication administration with drug references, such as the PDR (Physicians Desk Record), or similar, for immediate check of potential adverse drug interactions, inappropriate dose, and contraindications. The system provides alerts when drug interactions, inappropriate dose and contraindications are determined Treatment flow records may be linked to patient care reference information. The system might also reduce erroneous billing charges for medication and supplies, and assure billing of only the utilized resources, including medication and other care delivery products.

Further benefits of exemplary embodiments of the automatically synchronized, patient care coordination system include error reduction. The digital font format of information display on the screens of the hand-held computers improves legibility over handwriting and should reduce errors. Further, a screen for the patient may include a photo of the patient thereby reducing the potential for administering medications or treatment to the wrong patient. Medication may also be depicted pictorially in color, thereby reducing the potential for administration of the wrong dose of a medication, since tablets and pills are often color-coded and/or shape-configured to indicate the amount of active ingredient. The system may also use the clock applications program for example to provide an alert about an upcoming administration of a medication to a patient, as well as a missed scheduled medication. This should then allow appropriate remedial action and proper documentation by requiring explanatory input into the system.

Exemplary embodiments of the automatically synchronized, patient care coordination system eliminate duplication and attendant wasted resources. For example, once input, the patient's primary record may populate all appropriate fields eliminating need to rewrite information once entered. Thus, for example, resident name, room number, primary physician, allergies, diagnoses, and medication orders are all entered only once. Further, the entry of doctor's orders simultaneously creates several required documents, such as for example, the Physician's Order form, the Medication Administration Record, Treatment Records, and appropriate supplemental care records. The system may also transmit data to the dispensing pharmacy for prescribed medications.

Exemplary embodiments of the automatically synchronized, patient care coordination system support care decision-making. For example, the system may provide allergy checking with alerts, drug interaction checking, drug utilization evaluation, access to clinical references, graphic display of monitored data (such as patient/resident weight, temperature, pulse, blood pressure), reports interpreting compiled data for individual patients/residents, facility population, or other specified data elements. The system may also provide medication-related assessments, including but not limited to need for pulse monitoring or blood glucose results for determining an insulin dose to be administered. For example, the system may also record the direct care given by the Certified Nursing Assistant (CNA) which is required in the MDS billing. The system may also facilitate a guided narrative summary of care by including a capability to input dictated notes, which are converted to text using voice recognition technology.

Exemplary embodiments of the automatically synchronized, patient care coordination system support prompt care delivery and appropriate follow up. The system may provide these benefits through alerts for pending care events, such as monitoring needs, scheduled medications and treatments; Lists for specified data elements, such as pending lab specimen collection needs or needed vital signs monitoring; and Reports to monitor & evaluate care, pre-defined and user-defined parameters. Further, exemplary systems may provide lists to monitor and support care, using pre-defined and user-defined parameters and provide Care Summaries and change-of-shift reports, utilizing pre-defined and user-defined parameters.

While examples of embodiments of the technology have been presented and described in text and some examples also by way of illustration, it will be appreciated that various changes and modifications may be made in the described technology without departing from the scope of the inventions, which are set forth in and only limited by the scope of the appended patent claims, as properly interpreted and construed.

The invention claimed is:

1. An integrated patient care and billing coordination system, the system comprising:
   a plurality of hand-held computers, the hand-held computers each having a user interface, the user interface enabling activities comprising: facilitating access to patient health care information, inputting new patient health care information, receiving real-time information and alerts about patient health condition; notification of timing of patient prescription medication treatment, inputting of timing of administration of patient treatment and creating an electronic record confirming the timing of the treatment administered; and
   a computer in wireless communication with the plurality of hand-held computers, the computer having memory comprising a database configured to store and update patient health care information, the computer automatically and in real time receiving patient health care information from one of the plurality of hand-held computers and automatically synchronizing, in real time, the received patient health care information with all others of the plurality of hand-held computers, the computer in communication with an in-system party or an out-of-system party to transmit patient health care information and receive acknowledgment of receipt of the information, the computer monitoring fee-bearing information exchanged with the in-system party and updating the database for an appropriate patient;

wherein the patient health care information comprises, for each patient, prescriptions, care-giver notes, care-giver prepared charts, patient medical history, physician orders and patient health insurance information.

2. The system of claim 1, wherein the plurality of hand-held computers comprise tablet computers.

3. The system of claim 2, wherein the computer comprises either a remote server or comprises a cloud computing network.

4. The system of claim 1, further comprising accessibly stored information about pharmaceutical drugs, and software applications that cross check prescribed drugs for appropriate administration to a patient by checking against allergy indications, sensitivity indications and drug interactions for the patient.

5. The system of claim 1, wherein the in-system party is a pharmaceutical dispensing entity, and the fee-bearing information exchanged with the in-system party includes a prescription for a medication, a fee is automatically assessed based on the prescription, and the fee is recorded appropriately in the database.

6. The system of claim 1, wherein the plurality of hand-held computers are used by patient care providers in a health care facility, the patient health care information includes information about patient prescription drug administration, and the system is configured to provide a reminder to patient care providers via the hand-held computers about upcoming scheduled treatment activity.

7. The system of claim 1, wherein the plurality of hand-held computers each comprise a touch screen, the touch screens each comprise graphics relating to a generic patient health care provider environment, user touching of a selected graphic permitting user access to patient health care information suggested by the selected graphic.

8. The system of claim 1, further comprising receiving patient health care data input from patient care devices and storing these in the database for a corresponding patient.

9. The system of claim 8, wherein the patient health care data comprises patient vital signs and clinical information monitored automatically by patient care devices.

10. The system of claim 1, further comprising alerting a care giver about patient data from a patient care device when the patient care data is indicative of an unacceptable condition.

11. An integrated, synchronized patient care and billing coordination system, the system comprising:

a plurality of hand-held computers, the hand-held computers each having a user interface, the user interface enabling activities comprising: facilitating access to patient health care information, inputting new patient health care information, receiving real-time information and alerts about patient health condition; notification of timing of patient prescription medication treatment, inputting of timing of administration of patient treatment and creating an electronic record confirming the timing of the treatment administered; and a computer in real time communication with the plurality of hand-held computers, the computer having memory comprising a database configured to receive, store and update patient health care information for a plurality of patients, the computer automatically and in real time receiving patient health care information from one of the plurality of hand-held computers and automatically synchronizing, in real time, the received patient health care information with all others of the plurality of hand-held computers, the computer also receiving as input patient data from patient care devices and storing these data in the database for a corresponding patient, the computer transmitting patient health care information to an in-system pharmacy and receiving acknowledgment of the information, the computer monitoring fee-bearing information, automatically assessing a predetermined fee based on fee-bearing information exchanged with the in-system pharmacy, and automatically applying a charge to the database for a corresponding patient;

wherein the patient health care information comprises, for each patient, prescriptions, care-giver notes, care-giver prepared charts, patient medical history, physician orders and patient health insurance information.

12. The system of claim 11, wherein the plurality of hand-held computers comprise tablet computers.

13. The system of claim 12, wherein the computer comprises a remote server or a cloud computing network.

14. The system of claim 11, wherein the system further comprises communicating with an out-of-system pharmaceutical dispensing entity, and information communicated comprises fee-bearing information and a prescription for a medication.

15. The system of claim 11, further comprising accessibly stored information about pharmaceutical drugs, and software applications that cross check prescribed drugs for appropriate administration to a patient by checking against allergy indications, sensitivity indications and drug interactions for the patient.

16. The system of claim 11, wherein the plurality of hand-held computers are used by patient care providers in a health care facility, the patient health care information includes information about patient prescription drug administration, and the hand-held computer is configured to provide a reminder to patient care providers about upcoming scheduled prescription patient drug administration activity.

17. The system of claim 11, wherein the plurality of hand-held computers each comprise a touch screen, the touch screens each comprise graphics relating to a generic patient health care provider environment, user touching of a selected graphic permitting user access to patient health care information suggested by the selected graphic.

18. The system of claim 11, wherein the patient data from patient care devices comprises patient vital signs and clinical information monitored automatically by patient care devices.

19. The system of claim 18, further comprising alerting a care giver about patient data from a patient care device when the patient care data is indicative of an unacceptable condition.

20. A multi-user, automatically synchronized, patient care coordination system, the system comprising:

a plurality of wireless hand-held computers, the hand-held computers each having a user interface, the user interface enabling activities comprising: facilitating access to patient health care information, inputting new patient health care information, receiving real-time information and alerts about patient health condition; notification of timing of patient prescription medication treatment, inputting of timing of administration of patient treatment and creating an electronic record confirming the timing of the treatment administered; and at least one remote server, the remote server in real time communication with the plurality of hand-held computers in real time, the remote server having memory comprising a database configured to store patient health care information for a plurality of patients, and applications software, the remote server automatically and in real time synchronizing patient health care information between the plurality of portable hand-held computers by making newly-input patient health care information received from any one of the plurality of hand-held computers substantially immediately available to all others of the plurality of portable hand-held computers, the remote server in electronic digital communication with an in-system party or out-of-system party to transmit encrypted patient health care information to the in-system party or out-of-system party, system application software automatically assessing a fee based on patient health care information communicated to the in-system party or out-of-system party;

wherein the patient health care information comprises, for each patient, prescriptions, care-giver notes, care-giver prepared charts, patient medical history, physician orders and patient health insurance information.

\* \* \* \* \*